United States Patent [19]
Monte

[11] Patent Number: 5,578,336
[45] Date of Patent: Nov. 26, 1996

[54] CONFECTION CARRIER FOR VITAMINS, ENZYMES, PHYTOCHEMICALS AND AILMENTARY VEGETABLE COMPOSITIONS AND METHOD OF MAKING

[76] Inventor: Woodrow C. Monte, 6511 S. River Rd., #65, Tempe, Ariz. 85283

[21] Appl. No.: 475,551

[22] Filed: Jun. 7, 1995

[51] Int. Cl.⁶ ........................................................ A23L 1/30
[52] U.S. Cl. ............................. 426/72; 426/73; 426/103; 426/293; 426/297; 426/303; 426/304; 426/305; 426/311; 426/541; 426/660
[58] Field of Search ........................... 426/103, 72, 73, 426/293, 297, 303, 304, 305, 311, 541, 660

[56] References Cited

U.S. PATENT DOCUMENTS

| | | | |
|---|---|---|---|
| 1,859,206 | 5/1932 | Heisler | 426/660 |
| 2,508,477 | 5/1950 | Stievator et al. | 426/311 |
| 2,538,202 | 1/1951 | Kimball | 426/660 |
| 3,769,039 | 10/1973 | Kleinhert | 426/660 |

*Primary Examiner*—Helen Pratt
*Attorney, Agent, or Firm*—Tod R. Nissle, P.C.

[57] ABSTRACT

A confection includes a soft candy center containing from 5% to 40% by weight water. A first coating is applied to the candy center. A second coating is applied over the first coating. The second coating contains a vitamin, enzyme, phytochemical, or alimentary vegetable composition. The first coating seals moisture in the soft candy center to retard the biodegradation of the vitamin, enzyme, phytochemical or alimentary vegetable composition in the second coating.

26 Claims, 1 Drawing Sheet

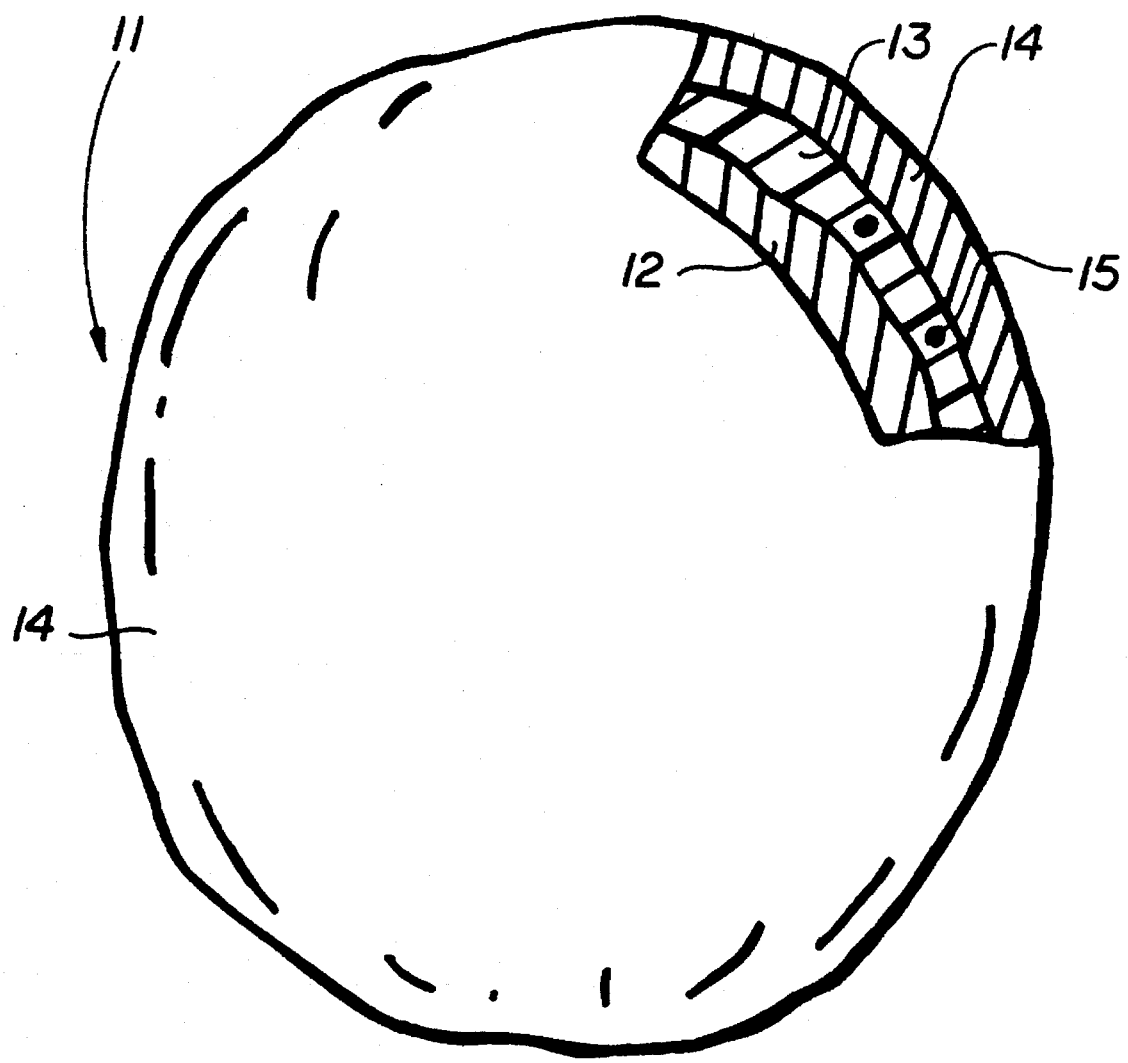

5,578,336

CONFECTION CARRIER FOR VITAMINS, ENZYMES, PHYTOCHEMICALS AND AILMENTARY VEGETABLE COMPOSITIONS AND METHOD OF MAKING

This invention relates to chewing gum and confections.

More particularly, the invention relates to chewing gum and confections which include vitaminic and enzymatic compositions and which, during storage of the gum and confections prior to their use, protect vitamins and enzymes from partial or complete biodegradation and decomposition and from spoilage due to contact with oxygen, water, and/in mineral compositions.

In another respect, the invention pertains to convenient methods for administering vitamins to humans, in which inconvenience or complications are reduced in comparison to conventional methods such as oral ingestion of tablets along with water or other drinking fluids or by parenteral injections.

In a further respect, the invention pertains to chewing gum and confections which arrange vitamins and enzymes in different coatings on the gum and confections to facilitate the efficient activation and utilization of the vitamins and enzymes by a human or other animal chewing the gum or the confections.

Vitamins and enzymes are essential for the efficient functioning of human beings and of other higher animals. Supplementing the diet by ingesting or parentally injecting artificially produced vitamins and enzymes is a common practice. However, parental injection or oral ingestion may, at the very least, be inconvenient. For example, many individuals either encounter difficulty in swallowing vitamin supplements or require liquid to ingest the vitamins. If a drinkable liquid is not available, then the individuals simply will not ingest the vitamin supplements.

Another problem with vitamin and enzyme supplements is that minerals, oxygen, and moisture found in such supplements act as catalysts which can rapidly promote the degradation, decomposition, and spoilage of vitamins and enzymes in the supplements. For example, the degradation in vitamin supplements of B vitamins such as thiamine can result in a disagreeable fish oil taste which causes a user to gag when ingesting the vitamin supplements or which causes gastrointestinal upset after ingestion. As a result, many individuals refuse to ingest vitamin and mineral supplements.

Accordingly, it would be highly desirable to provide more convenient compositions and methods for introducing supplement enzymes and vitamins into the human body. It would also be advantageous to provide such compositions and methods which reduce and minimize the rate at which enzymes and vitamins in the compositions degrade to produce unpleasant or potentially toxic by-products.

I have now discovered novel vitaminic, enzymatic, phytochemical, and ailmentary vegetable compositions in the form of chewing gum including a chewing gum composition; a first outer coating on the chewing gum; and, a second outer coating over the first coating and containing at least one vitamin, enzyme, phytochemical, and/or ailmentary vegetable composition. The second coating is substantially free of any minerals which promote the degradation of any vitamin, enzyme, phytochemical, and/or ailmentary vegetable composition in the second coating. The concentration of the vitamin, enzyme, phytochemical, or ailmentary vegetable composition in the second coating can vary as desired but is selected so as to be non-toxic to the individual utilizing the chewing gum composition.

The method of the invention comprises forming a coated chewing gum product and administering the gum to the mouth of a subject to be chewed. The chewing gum product includes a chewing gum composition including moisture; a first outer coating on the chewing gum composition and containing at least one vitamin, enzyme, phytochemical, and/or ailmentary vegetable composition; and, a second outer coating intermediate the gum composition and the first outer coating to sealingly separate the vitamin from the moisture in the chewing gum composition. The first outer coating is substantially free of minerals which promote the degradation of the vitamin. A coating is substantially free of a mineral when it contains less than about fifteen parts per million of the mineral, preferably less than about ten parts per million of the mineral.

I have also discovered novel vitaminic, enzymatic, phytochemical, and ailmentary vegetable compositions in the form of a confection including a soft candy center; a first outer coating on the soft candy center; and, a second outer coating over the first coating and containing at least one vitamin, enzyme, phytochemical, and/or ailmentary vegetable composition. The second coating is substantially free of any minerals which promote the degradation of any vitamin, enzyme, phytochemical, and/or ailmentary vegetable composition in the second coating. The concentration of the vitamin, enzyme, phytochemical, or ailmentary vegetable composition in the second coating can vary as desired but is selected so as to be non-toxic to the individual utilizing the confection. As used herein, the term soft candy center or soft candy composition refers to a center comprised of soft, chewable, ingestable candy selected from the group consisting of chocolate, caramels, toffees, jellies, gums (like the chewable sugar gum in the center of a jelly bean), creams, fudges, and marshmallows. Chewing gum is not ingestable and is not considered to comprise a soft candy center. Hard candies like fruit drops, mint, and brittle can not comprise a soft candy center. As used herein, the term candy refers to a sweet-tasting food which includes sugar or another sweetener as one of its main ingredients and which is produced by heating and then cooling a solution or mixture which includes the sweetener.

The method of the invention comprises forming a confection product and administering the confection product to the mouth of a subject to be chewed. The confection product includes a soft candy center composition including moisture; a first outer coating on the candy center composition and containing at least one vitamin, enzyme, phytochemical, and/or ailmentary vegetable composition; and, a second outer coating intermediate the candy center composition and the first outer coating to sealingly separate the vitamin from the moisture in the candy center composition. The first outer coating is substantially free of minerals which promote the degradation of the vitamin. A coating is substantially free of a mineral when it contains less than about fifteen parts per million of the mineral, preferably less than about ten parts per million of the mineral.

BRIEF DESCRIPTION OF THE DRAWING

A gum or confection manufactured in accordance with the invention is illustrated in the drawing.

Each outer coating 13, 14 on gum or confections 11 produced in accordance with the method of the invention can comprise one or more layers. At least one of the coatings typically comprises a plurality of hard and/or crunchy "pan" coating layers of a sugar or sugarless sweetener. The hard "pan" coating includes less than about 5% water by weight, preferably less than 3% water by weight, and normally less than about 2% water by weight. In the case of sugar sweetener coatings, corn syrup and other syrups have been employed. In the case of sugarless sweetener coatings, aqueous solutions of xylitol, mannitol, maltitol and sorbitol, also known as syrups, have been employed. Such syrups may contain additives such as moisture absorbing compounds 15, anti-adherent compounds, dispersing agents, film forming agents, binders and the like.

During the formation of "pan" coatings, each soft confection core (i.e., soft candy center) or gum pellet is typically covered with a sweetener syrup as its travels over a tray or conveyor along with other gum pellets or confection cores 12, or the gum pellet or confection core is tumbled with other gum pellets and confection cores in a large vessel or "pan" with syrup. A stream of warm air is directed onto the coated pellets to dry the coating. When the pellet is, in the latter case, in a "pan", more syrup is introduced after the pellet is dried, followed by further tumbling and drying. When the gum pellet or confection core is on a conveyor, the gum pellet or confection core can be covered by an additional layer of syrup and dried as the conveyor passes through subsequent processing stations. In this way a coating can be built up layer by layer to the desired thickness.

By way of example, and not limitation, a sweetener coating for 1000 gum pellets or confection cores weighing a total of about 1576 grams and having an average weight per unit of 1.58 grams can include sucrose or dextrose (1222 grams); oil of spearmint (1.1663 grams); pepsin essence (0.68 g); and, water.

The carrier utilized to form a vitamin coating on a gum pellet or confection core can be alcohol, can be the syrup used to form a hard "pan" coating, can be water, or can be any other suitable carrier which is non-toxic to a human being. While the carrier ordinarily is a liquid carrier, a powder or another desired carrier comprised of one or more solid components may be utilized. The liquid carrier for the vitamins is chosen with reference to the solubility and/or suspendibility of the vitamins and, for example, may be a non-toxic alcohol, water, or an aqueous alcohol. In one presently preferred embodiment of the invention, ethanol alcohol is the carrier. If the vitamin composition selected does not contain water-insoluble components, a water solution of the vitamins can be utilized.

A powder spray process can be utilized to apply a coating of a vitamin(s) or an enzyme(s). In the powder spray process a powder is suspended in a pressurized gas which is sprayed onto a surface. Using such a technique, the rate of application of a vitamin, enzyme, or phytochemical can be controlled by regulating the pressure of the gas, the amount of the vitamin, enzyme, or phytochemical suspended in the gas and the rate of travel of the chewing gum pellets or confection cores under the spray.

A solution spray process can be utilized to apply a coating of a vitamin, enzyme, or phytochemical. An aqueous solution is formed and then sprayed onto gum pellets or confection cores, or is sprayed as an aerosol mist onto an existing coating on the chewing gum pellets or confection cores.

Electrostatic deposition can be utilized to apply a coating of a vitamin, enzyme, or phytochemical. Particles are first charged and then are sprayed onto chewing gum pellets or confection cores or are sprayed onto a coating on the chewing gum pellet or on a confection cores which has an oppositely charged surface.

The vitamins which can be employed in the practice of the invention include complex organic substances which are found variously in most foods and which are essential, in small amounts, for the normal functioning of human beings. For example, such vitamins may include:

vitamin A, a fat-soluble aliphatic alcohol, $C_2OH_{29}OH$, found in fish-liver oil, egg yolk, butter, etc. This vitamin occurs in two forms, vitamin $A_1$ and $A_2$.

vitamin B (complex), a group of unrelated water-soluble substances including: (a) vitamin $B_1$ (thiamine); (b) vitamin $B_2$ (riboflavin); (c) vitamin $B_6$ (pyridoxine); (d) nicotinic acid; (e) pantothenic acid; (f) biotin (also called vitamin H); (g) inositol; (h)choline; (i) folic acid; and, vitamin $B_{12}$ (cyanocobalamine).

vitamin C, an organic compound $C_6H_3O_6$, occurring in citrus fruits, tomatoes and various vegetables.

vitamin D, any of several related vitamins occurring in fish-liver oils, milk, egg yolks, etc.; specifically, (a) vitamin $D_1$, a mixture of calciferol with another sterol prepared by the ultraviolet irradiation of ergosterol; (b) vitamin $D_2$ (calciferol); (c) vitamin $D_3$, a substance similar to vitamin $D_2$, found chiefly in fish liver oils.

vitamin E, a substance consisting of a mixture of tocopherols.

vitamin K, a vitamin occurring in certain green vegetables, fish meal, hempseed, etc. The two varieties of vitamin K are vitamin K1, found chiefly in alfalfa leaves, and vitamin K2, found chiefly in fish meal.

vitamin P, a mixture of the flavones occurring especially in citrus juice and paprika.

The enzymes which can be utilized in the practice of the invention include enzymes which are non-toxic to human beings, which facilitate the digestion and use by the human body of foods of food components such as vitamins, minerals, and other enzymes or which promote the cleansing of teeth and the oral cavity. For example, but not by way of limitation, such enzymes can include alpha amylase, protease, beta glucanase, glucoamylase, glucose oxidase, pectinase, xylanase, or other protein hydrolyzing enzymes, starch dextrinizing enzymes, starch saccharifying enzymes, and/or cellulose hydrolyzing enzymes.

Phytochemicals can also be utilized in the practice of the invention. Phytochemicals include sulphoraphane, PEITC (phenethylisothiocyanate), indole-3-carbinol, aurones, chalcones, anthocyanidins, flavanones, anthocyanidins, flavones, flavonols, flavan 3-ols, oligomeric flavonoids, biflavonoids, isoflavonoids and other compounds which are, prior to being harvested, stored in the epidermal cells of plants and which typically absorb light having wavelengths in the range 10 to 800 nm.

Ailmentary vegetable compositions can also be utilized in the practice of the invention. An ailmentary vegetable composition as used herein is a vegetable or a part of a vegetable which alleviates, prevents, or remedies an impairment of the normal state of a human being that interrupts or modifies the performance of the vital functions of the human being, such impairment being a response to a specific infective agent factor (as worms, bacteria, or viruses) or to a combination of these factors. A vegetable is an organism typically characterized by lack of locomotive movement (absence of locomotion and of special organs of sensation and digestion) or rapid motor response, by absence of obvious nervous or sensory organs though possessing irritability as indicated by specific response to stimuli, by possession of cell walls composed of cellulose, and by a nutritive system in which carbohydrates are formed photosynthetically through the action of chlorophyll and organic nutrients are not required, and exhibiting a strong tendency to alternation of a sexual with an asexual generation though one or the other may be greatly modified or almost wholly suppressed. Vegetable parts can be produced by any desired means including without limitation mechanical means, such as, for example, by grinding or cutting leaves or seeds or stems to produce a vegetable part comprised of such cut or comminuted leaves or seeds; including chemical means, such as by extraction by boiling seeds, stems, etc. in water to extract a particular component from the seeds, etc. into solution or dispersion in the water, or by contacting a vegetable component such as, for example, a leaf with a liquid, gaseous, or dry composition which interacts with the leaf to extract and/or separate a particular component or components from the left to produce a vegetable part including the extracted or separated component or components; and, including heat, electrical, or other means. Ailmentary vegetable compositions are medicaments and do not include vegetables or vegetable parts which function only as food. Examples of ailmentary vegetable compositions include a cayenne powder made from drying and grinding the whole seeds of the vegetable *Capsicum frutescens longum*; a sedative powder made from drying and grinding the root of the vegetable *Valeriana officinalis*; powder made the flow heads of vegetables of the genus Anthemis, such flower heads containing a diaphoretic and antispasmodic composition; an antiseptic oil containing thymol and carvacrol which is produced from vegetables of the genus Thymus; an aqueous solution produced by boiling the vegetable *Nepeta Cataria*, a member of the family Labiatae, in water; and, an oil obtained by the stream distillation of a vegetable of the genus Allium.

Vitamins, enzymes, phytochemicals, and ailmentary vegetable compositions can be admixed, dissolved, or dispersed in water, ethanol, or any other powder, liquid, or gas carrier to form a coating mixture which can be applied to a gum composition pellet, to a coating on a gum composition pellet, to a confection core, or to a coating on a confection core, and if necessary dried, in order to form a coating layer which includes or comprises in whole a vitamin, enzyme, phytochemical, or an ailmentary vegetable composition. Ethanol is, when appropriate, often a desired carrier because it quickly evaporates after being applied to a gum composition pellet or confection core or after being applied to an existing coating on a gum composition or confection.

The chewing gum composition utilized in the practice of the invention is formulated from standard ingredients and by known methods in the art. The composition ordinarily is comprised of a gum base and additives such as a sweetener, flavoring, fillers, etc. The gum base typically comprises from 5% to about 50% by weight of the chewing gum composition. Plasticizers or softeners are often are incorporated into the gum base in a concentration of from about 3% to 25% by weight, typically of from about 3% to about 6%. By way of example, the sweetener can comprise water-soluble naturally occurring agents such as monosaccharides, disaccharides, etc.; can comprise a water soluble artificial sweetener such as a soluble saccharin salt, etc.; and/or can comprises a dipeptide sweeteners such as L-aspartyl L-phenylalanine methyl ester. The water-soluble naturally occurring sweeteners typically comprise from about 0.01% to 90% by weight of the gum composition, preferably from 25% to 75% by weight. The water soluble artificial sweeteners and dipeptide sweeteners typical comprise from 0.005% to 5.0%, preferably about 0.05% to about 2.5% of the chewing gum composition. Coloring agents, fillers, and flavoring agents can also be included in the chewing gum composition.

The soft candy center composition utilized in the practice of the invention is formulated from standard ingredients and by known methods in the art. For example, chocolate candy centers consist mainly of roasted cacao beans, cacao butter, and sugar. These ingredients are mixed and then ground into a power. The powder is subjected to further grinding processes which produce heat. The heat melts the cacao butter. When the cacao butter melts, melted chocolate is formed. The melted chocolate is poured into molds and hardens. Soft candy centers comprised of chocolate shells filled with liquid, cream, etc. can be produced. Other examples of soft candy centers are caramels and toffees. In order to produce caramels and toffees, milk is cooked with sugars and vegetable fats. A flavoring is added to the cooked mixture, after which the mixture is cooled and cut into pieces. Still other examples of soft candy centers are jellies and gums. In order to produce jellies and gums, a solution of sugars is boiled. Flavoring, color, and a jelling agent are mixed into the solution to form a mold mixture. The jelling agent typically is a gelatin or starch. The mold mixture is poured into molds and sets.

The following examples are presented as non-limiting illustrations depicting the presently preferred embodiments of the invention.

EXAMPLE 1

Gum base (26% by weight), 40 Be corn syrup (15% by weight), and pulverized sugar (58% by weight) are blended to produce a gum mixture. Peppermint flavoring (1%) is added and blended into the gum mixture to produce a homogeneous chewing gum composition. The homogenous chewing gum composition is cooled, dusted, rolled into sheets, is scored to form a sheet of rectangular gum centers or cores. The scored sheet is broken up into individual gum cores.

EXAMPLE 2

A coating syrup is prepared by blending water (24% by weight), starch (0.9% by weight), and fine granulated sugar (75.1% by weight) until the coating syrup has a Baume value between 33 and 37.

EXAMPLE 3

A coating formulation is prepared by mixing the ingredients indicated in Table I into the alcohol carrier until they are dissolved and/or suspended and dispersed in the carrier.

TABLE I

| Ingredient | Parts by Weight |
| --- | --- |
| Carrier alcohol (200 proof spirit) | 87.903 |
| Peppermint flavoring oil | 3.1 |
| Glycerine | 2.16 |
| Emulsifier (Tween-80) | 0.16 |
| Fructose (flavoring agent) | 2.08 |
| Ascorbic acid | 2.15 |
| Vitamin E | 1.08 |
| Niacinamide | 0.72 |
| Pantothenic acid | 0.34 |
| Vitamin A | 0.12 |
| Pyridoxine hydrochloride | 0.072 |
| Riboflavin | 0.061 |
| Thiamine hydrochloride | 0.054 |
| Cyanocobalamine | 0.000093 |

EXAMPLE 4

A coating syrup is prepared by blending the ingredients in Table II until the coating syrup has a Baume value between 33 and 37.

TABLE II

| Ingredient | Parts by Weight |
| --- | --- |
| Water | 24.00 |
| Starch | 0.9 |
| Fine granulated sugar | 63.1 |
| Peppermint flavoring oil | 3.1 |
| Glycerine | 2.16 |
| Emulsifier (Tween-80) | 0.16 |
| Fructose (flavoring agent) | 2.08 |
| Ascorbic acid | 2.15 |
| Vitamin E | 1.08 |
| Niacinamide | 0.72 |
| Pantothenic acid | 0.34 |
| Vitamin A | 0.12 |
| Pyridoxine hydrochloride | 0.072 |
| Riboflavin | 0.061 |
| Thiamine hydrochloride | 0.054 |
| Cyanocobalamine | 0.000093 |

EXAMPLE 5

Ten grams of a four hundred gram sample of freshly cut broccoli grown out-of-doors is, after the broccoli is carefully washed in warm water, tested to determine the concentration of sulphoraphane, PEITC (phenethylisothiocyanate), and indole-3-carbinol in the broccoli. The broccoli is ripe and is free from insect and other damage. The remaining three hundred and ninety gram portion of the sample is subjected at room temperature to artificial light including a spectrum of light waves having wavelengths of from 260 to 400 nm (nanometers) for twenty-four consecutive hours at an intensity of 500 lumens per square foot. Twenty grams of the three hundred and ninety gram portion of the sample is then tested for the concentration of sulphoraphane, PEITC, and indole-3-carbinol. The concentration in weight of sulphoraphane, PEITC, and indole-3-carbinol per gram of broccoli of the twenty gram sample increases by over one hundred percent in comparison to the concentration of sulphoraphane, PEITC, and indole-3-carbinol in the freshly cut broccoli before the broccoli was subjected to the 260 to 400 nm light for twenty-four hours.

EXAMPLE 6

One hundred grams of the 390 gram portion of the sample subjected to artificial sunlight in Example 5 is ground to one hundred mesh and is contacted with five grams of cellulase enzyme for three hours to form an extraction mixture. The cellulase enzyme promotes the breaching of cell walls to release sulphoraphane, PEITC (phenethylisothiocyanate), and indole-3-carbinol in the broccoli.

EXAMPLE 7

Twenty five grams of the extraction mixture of Example 6 is mixed for an hour with twenty-five grams of DMSO-d6 to extract the sulphoraphane, PEITC, and indole-3-carbinol into the DMSO. After the hour has elapsed, the DMSO-d6 is separated from the extraction mixture. The DMSO-d6 carries sulphoraphane, PEITC, and indole-3-carbinol.

EXAMPLE 8

Twenty five grams of the extraction mixture of Example 6 is mixed with twenty-five grams of ethanol at room temperature for one hour to extract sulphoraphane, PEITC, and indole-3-carbinol from the extraction mixture into the ethanol. After the hour has elapsed, the ethanol is separated from the extraction mixture to product an ethanol phytochemical byproduct solution. The ethanol byproduct solution carriers sulphoraphane, PEITC, and indole-3-carbinol.

EXAMPLE 9

Examples 6 to 8 are repeated except that in Example 6 five grams of beta amylase enzyme is substituted for the five grams of cellulase enzyme. Similar results are obtained. The amylase enzyme promotes breakdown of cellular walls.

EXAMPLE 10

Example 6 to 8 are repeated except that in Example 6 five grams of lipase enzyme is substituted for the five grams of cellulase enzyme. Similar results are obtained. The lipase enzyme promotes breakdown of cellular walls.

EXAMPLE 11

Examples 6 to 8 are repeated except that in Example 6 five grams of protease enzyme is substituted for the five grams of cellulase enzyme. Similar results are obtained. The protease enzyme promotes breakdown of cellular walls.

EXAMPLE 12

Examples 5 to 8 are repeated, except that broccoli purchased from the produce department of a Smith's supermarket in Phoenix, Arizona is substituted for the fresh cut broccoli. The broccoli is standard store broccoli, has not dried, consists in large part of living broccoli cells, is maintained in a cooled produce area, and is intermittently sprayed with water by store personnel. The store broccoli is ripe and is free from insect and other damage. Similar results are obtained in each of Examples 5 to 8.

EXAMPLE 13

Ten grams of a four hundred gram sample of epidermal tissue from freshly picket Thompson Seedless grapes grown out-of-doors is, after the grapes are all carefully washed with warm water, tested to determine the total concentration of chemical compounds including aurones, chalcones, anthocyanidins, flavanones, anthocyanidins, flavones, flavonols, flavan 3,4-diols, oligomeric flavonoids, biflavonoids, and isoflavonoids in the epidermal tissue. The grapes are ripe and juicy, are free from insect damages, and are not bruised. The remaining three hundred and ninety gram portion of the sample is subjected to artificial light including a wavelength of 302 nm (nanometer) for one hour at an intensity of one lumen per square foot. Twenty grams of the three hundred and ninety gram portion of the sample is then tested for the total concentration of the aurones, chalcones, anthocyanidins, flavanones, anthocyanidins, flavones, flavonols, flavan 3-ols, oligomeric flavonoids, biflavonoids, and isoflavonoids in the grape. The total concentration in weight of aurones, chalcones, anthocyanidins, flavanones, anthocyanidins, flavones, flavonols, flavan 3-ols, oligomeric flavonoids, biflavonoids, and isoflavonoids per gram of grapes in the twenty gram sample increases by over one hundred percent in comparison to the concentration of the same compounds in the grapes before the grapes were subjected to the 302 nm light for one hours. The length of time during which the sample is exposed to the 302 nm light can vary as desired. Increasing the length of time appears to increase the concentration of the aurones, chalcones, etc. in the sample.

EXAMPLE 14

One hundred grams of the 390 gram portion of the sample of grapes in Example 13 which was subjected to the 302 nm light is ground to one mesh and is contacted with five grams of cellulase enzyme for three hours at room temperature to form an extraction mixture.

EXAMPLE 15

Twenty-five grams of the extraction mixture of Example 14 is mixed for an hour at room temperature with twenty five grams of DMSO-d6 to extract aurones, chalcones, anthocyanidins, flavanones, flavones, flavonols, flavan 3,4-diols, oligomeric flavonoids, biflavonoids, and isoflavonoids into the DMSO. After the hour has elapsed, the DMSO-d6 is separated from the extraction mixture. The DMSO-d6 carries aurones, chalcones, anthocyanidins, flavanones, anthocyanidins, flavones, flavonols, flavan 3,4-diols, oligomeric flavonoids, biflavonoids, and isoflavonoids.

EXAMPLE 16

Twenty-five grams of the extraction mixture of Example 14 is mixed with twenty five grams of ethanol at room temperature for one hour to extract aurones, chalcones, anthocyanidins, flavanones, flavones, flavonols, flavan 3,4-diols, oligomeric flavonoids, biflavonoids, and isoflavonoids from the extraction mixture into the ethanol. After the hour has elapsed, the ethanol is separated from the extraction mixture to produce an ethanol byproduct phytochemical solution. The ethanol byproduct solution carries aurones, chalcones, anthocyanidins, flavanones, anthocyanidins, flavones, flavonols, flavan 3-ols, oligomeric flavonoids, biflavonoids, and isoflavonoids.

EXAMPLE 17

Examples 13 to 16 are repeated except that the artificial light used in Example 13 has a spectrum of wavelengths in the range of 400 to 800 nm and an illuminescence of 20,000 lumens per square foot. Similar results are obtained.

EXAMPLE 18

Examples 13 to 16 are repeated except that the light used in Example 13 has an intensity of 100 lumens per square foot. Similar results are obtained.

EXAMPLE 19

Examples 13 to 16 are repeated except that the light used in Example 13 has an intensity of five lumens per square foot. Similar results are obtained. One or more wavelengths of artificial light can be utilized to illuminate one or more parts of a plant in order to increase the concentration of a light absorbing compound in the plant. The illuminescence of the light can be adjusted as desired, as can the time the plant is exposed to the light. In some cases, it might be desirable to expose a plant to a single wavelength of light in the range of 260 to 800 nm for a minute or less at a small illuminescence of one lumen per square foot. This could be the case when it is desired to increase the concentration in a plant of one or more particular light absorbing compounds. In another case, it might be desirable to expose a plant to artificial light containing a spectrum of wavelengths in the range of 260 to 800 nm and at a high illuminescense greater than 10,000 lumens per square foot for twenty-four hours or more. The wavelength, illuminescence, and length of time the plant is exposed to the artificial light preferably, but not necessarily, are selected to that the plant is not burned or otherwise damaged.

EXAMPLE 20

Examples 13 to 19 are repeated except that in Example 13 400 grams of epidermal tissue from freshly picked apricots are carefully washed with warm water and substituted for the 400 grams of grapes. The apricots are ripe and juicy, are not bruised, and are free from insect damage. Similar results are obtained.

EXAMPLE 21

Examples 13 to 19 are repeated except that in Example 13 400 grams of freshly picked carrots are carefully washed with warm water and are substituted for the 400 grams of grape epidermal tissue. The carrots are ripe, are free from insect and other damage. Similar results are obtained.

EXAMPLE 22

Example 20 is repeated except that epidermal tissue from apricots purchased from the produce department of a Smith's supermarket in Phoenix, Arizona are carefully washed with warm water and are substituted for the freshly picked apricots. The apricots are standard store apricots, are ripe and juicy, have not been dried, consist in large part of living apricot cells, and were maintained in a cooled produce area in the store. Similar results are obtained.

EXAMPLE 23

Pea leaf tendrils grown in continuous light including light having a spectrum of wavelengths of from 400 to 800 nm were tested to determine the total topographic distribution (the "Total Quantity") in umoles per g fr wt of the group of chemical compounds including aurones, chalcones, anthocyanidins, flavanones, flavones, flavonols, flavan 3,4-diols, oligomeric flavonoids, biflavonoids, and isoflavonoids. The results are shown below in TABLE I. Each sample noted in TABLE III was extracted from about ten milligrams of tendril tissue.

TABLE III

| Part of Tendril | Total Quantity umoles per g fr wt |
|---|---|
| Apical fourth | 7.21 + 0.07 |
| Second fourth | 5.62 + 0.81 |
| Third fourth | 3.10 + 0.20 |
| Basal fourth | 1.86 + 0.07 |

EXAMPLE 24

An enzyme coating syrup is prepared by blending the ingredients in Table IV until the coating syrup has a Baume value between 33 and 37.

TABLE IV

| Ingredient | Parts by Weight |
|---|---|
| Water | 28.45 |
| Starch | 0.9 |
| Fine granulated sugar | 63.1 |
| Peppermint flavoring oil | 3.1 |
| Glycerine | 2.16 |
| Emulsifier (Tween-80) | 0.16 |

TABLE IV-continued

| Ingredient | Parts by Weight |
| --- | --- |
| Fructose (flavoring agent) | 2.08 |
| TENASE-1200 (alpha amylase) (Produced by Solvay Enzymes, Inc.) | 0.01 |

The amount of alpha amylase enzyme in the coating syrup can vary as desired, but typically is in a range which produces a desired coating having about 0.0001 to 0.3 percent by weight of the enzyme.

EXAMPLE 25

A enzyme coating syrup is prepared by blending the ingredients in Table V until the coating syrup has a Baume value between 33 and 37.

TABLE V

| Ingredient | Parts by Weight |
| --- | --- |
| Water | 28.45 |
| Starch | 0.9 |
| Fine granulated sugar | 63.1 |
| Peppermint flavoring oil | 3.1 |
| Glycerine | 2.16 |
| Emulsifier (Tween-80) | 0.16 |
| Fructose (flavoring agent) | 2.08 |
| Protease enzyme | 0.04 |

The amount of protease enzyme in the coating syrup can vary as desired, but typically is a range which produces a dried coating having about 0.0001 to 0.3 percent by weight of the enzyme.

EXAMPLE 26

Fifty grams of TENASE-1200 (alpha amylase) powder is provided.

EXAMPLE 27

A coating formulation is prepared by mixing the ingredients indicated in Table VI into the alcohol carrier until they are dissolved and/or suspended and dispersed in the carrier.

TABLE VI

| Ingredient | Parts by Weight |
| --- | --- |
| Carrier alcohol (200 proof spirit) | 87.903 |
| Peppermint flavoring oil | 3.1 |
| Glycerine | 2.16 |
| Emulsifier (Tween-80) | 0.16 |
| Fructose (flavoring agent) | 2.08 |
| Ethanol byproduct phytochemical solution of Example 16 herein* | 5.50 |

*Ethanol byproduct solution carries aurones, chalcones, anthocyanidins, flavanones, anthocyanidins, flavones, flavonols, flavan 3-ols, oligomeric flavonoids, biflavonoids, and isoflavonoids.

The amount of the ethanol byproduct phytochemical solution in the coating formulation can be varied as desired.

EXAMPLE 28

A coating formulation is prepared by mixing the ingredients indicated in Table VII into the alcohol carrier until they are dissolved and/or suspended and dispersed in the carrier.

TABLE VII

| Ingredient | Parts by Weight |
| --- | --- |
| Carrier alcohol (200 proof spirit) | 87.903 |
| Peppermint flavoring oil | 3.1 |
| Glycerine | 2.16 |
| Emulsifier (Tween-80) | 0.16 |
| Fructose (flavoring agent) | 2.08 |
| Ethanol byproduct phytochemical solution of Example 8 herein* | 5.50 |

*Ethanol byproduct solution carries sulphoraphane, PEITC, and indole-3-carbinol.

The amount of the ethanol byproduct phytochemical solution in the coating formulation can be varied as desired.

EXAMPLE 29

Gum cores from Example 1 to be coated are put in a conventional revolving coating pan. Cool dry air is used to dedust the gum cores. The coating syrup of Example 2 is heated to 78 degrees Centigrade. The cores are coated with coating layers five times with the syrup for about a minute each. After each coating layer is applied, the cores are dried for about three and a half minutes at approximately thirty-two degrees C by blowing air over the cores. Each time the cores are dried, a smooth hard layer is formed. The number of coating layers of the syrup applied to the gum cores can vary as desired. A plurality of coating layers are typically applied to increase the sealing effect of the resulting coatings to prevent moisture from penetrating the coating and contacting vitamins, enzymes, or phytochemicals subsequently applied to the gum cores.

EXAMPLE 29A

Example 29 is repeated, except the gum cores are replaced by soft candy centers consisting of chocolate. Similar results are obtained.

EXAMPLE 29B

Example 29 is repeated, except the gum cores are replaced by soft candy centers consisting of gum of the type found in the center of jelly beans. Similar results are obtained.

EXAMPLE 30

Coated gum cores from Example 29 which are to receive additional coating layers are put in a conventional revolving coating pan. The vitamin enhanced coating alcohol formulation of Example 3 is heated to about seventy degrees C. The cores are coated with coating layers two times with the syrup for about a minute and a half each. After each coating layer is applied, the cores are dried for about two minutes at approximately thirty degrees C by blowing air over the cores. The number of layers of the coating formulation applied to the gum cores can vary as desired.

EXAMPLE 30A

Example 30 is repeated, except that the coated candy centers from Example 29A are utilized in place of the coated gum cores. Similar results are obtained.

EXAMPLE 30B

Example 30 is repeated, except that the coated candy centers from Example 29B are utilized in place of the coated gum cores. Similar results are obtained.

EXAMPLE 31

Coated gum cores from Example 30 which are to receive additional coating layers are put in a conventional revolving coating pan. The coating syrup of Example 2 is heated to about eighty degrees C. Ten coating layers of the heated syrup are applied to the gum cores. After each of the ten coating layers is applied, the cores are dried for about four minutes at approximately thirty degrees C by blowing air over the cores. Each time the cores are dried, a smooth hard layer is formed.

EXAMPLE 31A

Example 31 is repeated, except that the coated candy centers from Example 30A are utilized in place of the coated gum cores. Similar results are obtained.

EXAMPLE 31B

Example 31 is repeated, except that the coated candy centers from Example 30B are utilized in place of the coated gum cores. Similar results are obtained.

EXAMPLE 32

Coated gum cores from Example 29 which are to receive additional coating layers are put in a conventional revolving coating pan. The vitamin enhanced coating syrup of Example 4 is heated to about eighty degrees C. One coating layer of the heating syrup is applied to the gum cores for about a minute and a half. After the coating is applied, the cores are dried for about four minutes at approximately thirty degrees C by blowing air over the cores. Each time the cores are dried a hard layer is formed.

EXAMPLE 32A

Example 32 is repeated, except that the coated candy centers from Example 29A are utilized in place of the coated gum cores. Similar results are obtained.

EXAMPLE 32B

Example 32 is repeated, except that the coated candy centers from Example 29B are utilized in place of the coated gum cores. Similar results are obtained.

EXAMPLE 33

Coated gum cores from Example 32 which are to receive additional coating layers are put in a conventional revolving coating pan. The coating syrup of Example 2 is heated to about eighty degrees C. Five coating layers of the heated syrup are applied to the cores. After each of the five coating layers is applied, the cores are dried for about four minutes at approximately thirty degrees C by blowing air over the cores. Each time the cores are dried a smooth hard layer is formed.

EXAMPLE 33A

Example 33 is repeated, except that the coated candy centers from Example 32A are utilized in place of the coated gum cores. Similar results are obtained.

EXAMPLE 33B

Example 33 is repeated, except that the coated candy centers from Example 32B are utilized in place of the coated gum cores. Similar results are obtained.

EXAMPLE 34

Coated gum cores from Example 29 which are to receive additional coating layers are put in a conventional revolving coating pan. One coating layer of the ethanol phytochemical byproduct solution of Example 8 is sprayed or misted onto the gum cores for about twenty seconds at a room temperature of about twenty-four degrees C. After the mist coating is applied, the cores are dried for about four minutes at approximately thirty degrees C by blowing air over the cores.

EXAMPLE 34A

Example 34 is repeated, except that the coated candy centers from Example 29A are utilized in place of the coated gum cores. Similar results are obtained.

EXAMPLE 34B

Example 34 is repeated, except that the coated candy centers from Example 29B are utilized in place of the coated gum cores. Similar results are obtained.

EXAMPLE 35

Coated gum cores from Example 34 which are to receive additional coating layers are put in a conventional revolving coating pan. The coating syrup of Example 2 is heated to about eighty degrees C. Ten coating layers of the heated syrup are applied to the cores. After each of the ten coating layers is applied, the cores are dried for about four minutes at approximately thirty degrees C by blowing air over the cores. Each time the cores are dried, a smooth, hard layer is formed. If it is desired herein to reduce the exposure of vitamins, enzymes, phytochemicals, or ailmentary vegetable compositions to temperatures above room temperature, then the temperature to which a coating syrup is heated prior to application over a coating layer containing vitamins, etc. can be reduced and, if appropriate, the viscosity of the coating syrup can be reduced by adding water, by using alcohol, or by any other desired means. The coating syrups utilized to form coating layers on gum cores in the practice of the invention can comprise natural or artificial sweeteners or can comprise in whole or in part any desired components other than sweeteners.

EXAMPLE 35A

Example 35 is repeated, except that the coated candy centers from Example 34A are utilized in place of the coated gum cores. Similar results are obtained.

EXAMPLE 35B

Example 35 is repeated, except that the coated candy centers from Example 34B are utilized in place of the coated gum cores. Similar results are obtained.

EXAMPLE 36

Coated gum cores from Example 29 which are to receive additional coating layers are put in a conventional revolving coating pan. Three coating layers of the ethanol byproduct solution of Example 16 are misted onto the gum cores at a room temperature of about 32 degrees C. After each the coating is applied for about twenty seconds, the cores are dried for about four minutes at approximately thirty degrees C by blowing air over the cores.

EXAMPLE 36A

Example 36 is repeated, except that the coated candy centers from Example 29A are utilized in place of the coated gum cores. Similar results are obtained.

EXAMPLE 36B

Example 36 is repeated, except that the coated candy centers from Example 29B are utilized in place of the coated gum cores. Similar results are obtained.

EXAMPLE 37

Coated gum cores from Example 36 which are to receive additional coating layers are put in a conventional revolving coating pan. The coating syrup of Example 2 is heated to about eighty degrees C. Twelve coating layers of the heated syrup are applied to the cores. After each of the twelve coating layers is applied, the cores are dried for about four minutes at approximately thirty degrees C by blowing air over the cores. Each time the cores are dried, a smooth, hard layer is formed.

EXAMPLE 37A

Example 37 is repeated, except that the coated candy centers from Example 36A are utilized in place of the coated gum cores. Similar results are obtained.

EXAMPLE 37B

Example 37 is repeated, except that the coated candy centers from Example 36B are utilized in place of the coated gum cores. Similar results are obtained.

EXAMPLE 38

Coated gum cores from Example 29 which are to receive additional coating layers are put in a conventional revolving coating pan. The enzyme coating syrup of Example 24 is heated to about sixty degrees C. Four coating layers of the enzyme coating syrup of Example 24 are applied to the gum cores. After each of the coatings is applied for about one and a half minutes, the cores are dried for about four minutes at approximately thirty degrees C by blowing air over the cores.

EXAMPLE 38A

Example 38 is repeated, except that the coated candy centers from Example 29A are utilized in place of the coated gum cores. Similar results are obtained.

EXAMPLE 38B

Example 38 is repeated, except that the coated candy centers from Example 29B are utilized in place of the coated gum cores. Similar results are obtained.

EXAMPLE 39

Coated gum cores from Example 38 which are to receive additional coating layers are put in a conventional revolving coating pan. The coating syrup of Example 2 is heated to about eighty degrees C. Twelve coating layers of the heated syrup are applied to the cores. After each of the twelve coating layers is applied, the cores are dried for about four minutes at approximately thirty degrees C by blowing air over the cores. Each time the cores are dried, a smooth hard layer is formed.

EXAMPLE 39A

Example 39 is repeated, except that the coated candy centers from Example 38A are utilized in place of the coated gum cores. Similar results are obtained.

EXAMPLE 39B

Example 39 is repeated, except that the coated candy centers from Example 38B are utilized in place of the coated gum cores. Similar results are obtained.

EXAMPLE 40

Examples 38 and 39 are repeated, except that the enzyme coating syrup of Example 25 is utilized instead of the enzyme coating syrup of Example 24. Similar results are obtained.

EXAMPLE 40A

Examples 38A and 39A are repeated, except that the enzyme coating syrup of Example 25 is utilized instead of the enzyme coating syrup of Example 24. Similar results are obtained.

EXAMPLE 40B

Examples 38B and 39B are repeated, except that the enzyme coating syrup of Example 25 is utilized instead of the enzyme coating syrup of Example 24. Similar results are obtained.

EXAMPLE 41

Coated gum cores from Example 29 which are to receive additional coating layers are put in a conventional revolving coating pan. The coating syrup of Example 2 is heated to about eight degrees C and one layer of the syrup is applied to the gum cores from Example 29. The syrup is dried until its surface is sticky (about a three minute drying period while blowing air at thirty degrees) whereupon the fifty grams of TENASE-1200 (alpha amylase) enzyme powder from Example 26 is added and blended for about two minutes until the syrup completely dries. The enzyme powder adheres to and is assimilated by the sticky syrup before the syrup dries.

EXAMPLE 41A

Example 41 is repeated, except that the coated candy centers from Example 29A are utilized in place of the coated gum cores. Similar results are obtained.

EXAMPLE 41B

Example 41 is repeated, except that the coated candy centers from Example 29B are utilized in place of the coated gum cores. Similar results are obtained.

EXAMPLE 42

Coated gum cores from Example 41 which are to receive additional coating layers are put in a conventional revolving coating pan. The coating syrup of Example 2 is heated to about eighty degrees C. Twelve coating layers of the heated syrup are applied to the cores. After each of the twelve coating layers is applied, the cores are dried for about four minutes at approximately thirty degrees C by blowing air over the cores. Each time the cores are dried, a hard layer is formed.

EXAMPLE 42A

Example 42 is repeated, except that the coated candy centers from Example 41A are utilized in place of the coated gum cores. Similar results are obtained.

EXAMPLE 42B

Example 42 is repeated, except that the coated candy centers from Example 41B are utilized in place of the coated gum cores. Similar results are obtained.

EXAMPLE 43

Examples 36 and 37 are repeated except that the coating formulation of Example 27 is utilized in place of the ethanol byproduct solution of Example 16. Similar results are obtained.

EXAMPLE 43A

Examples 36A and 37A are repeated, except that the coating formulation of Example 27 is utilized in place of the ethanol byproduct solution of Example 16. Similar results are obtained.

EXAMPLE 43B

Examples 36A and 37A are repeated, except that the coating formulation of Example 27 is utilized in place of the ethanol byproduct solution of Example 16. Similar results are obtained.

EXAMPLE 44

Examples 36 and 37 are repeated except that the coating formulation of Example 28 is utilized in place of the ethanol byproduct solution of Example 16. Similar results are obtained.

EXAMPLE 44A

Examples 36A and 37A are repeated, except that the coating formulation of Example 28 is utilized in place of the ethanol byproduct solution of Example 16. Similar results are obtained.

EXAMPLE 44B

Examples 36B and 37B are repeated, except that the coating formulation of Example 27 is utilized in place of the ethanol byproduct solution of Example 16. Similar results are obtained.

EXAMPLE 45

Fifty grams of cayenne powder is provided. The powder is made from drying and grinding the whole seeds of the vegetable *Capsicum frutescens longum*.

EXAMPLE 46

Examples 41 and 42 are repeated, except the fifty grams of cayenne powder from Example 45 is utilized in place of the fifty grams of TENASE-1200. Similar results are obtained.

EXAMPLE 46A

Examples 41A and 42A are repeated, except the fifty grams of cayenne powder from Example 45 is utilized in place of the fifty grams of TENASE-1200. Similar results are obtained.

EXAMPLE 46B

Examples 41B and 42B are repeated, except the fifty grams of cayenne powder from Example 45 is utilized in place of the fifty grams of TENASE-1200. Similar results are obtained.

By forming a first coating (having one or more coating layers) which is intermediate the gum core (or candy center) and a second coating (having one or more layers) that contacts the first coating, any moisture sensitive substances in the second coating are protected and sealed from moisture in the gum core or the candy center. Such moisture sensitive substances in the second coating can include vitamins, enzymes, phytochemicals, and ailmentary vegetable compositions. Similarly, by applying a third coating (having one or more coating layers) which extends over and contacts the second coating (but does not contact the first coating which is intermediate the second coating and the gum core or the candy center), any oxygen sensitive substances in the second coating are protected and sealed from oxygen in the ambient air. Such oxygen sensitive substances can include vitamins, enzymes, phytochemicals, and ailmentary vegetable compositions.

Any desired combination of vitamin, enzyme, and phytochemical coatings can be utilized. For example, the first coating (applied directly onto the gum core or candy center) on a gum core or candy center can comprise a hard sugar coating; the second coating (applied over and contacting the first coating) can comprise a hard sugar vitamin-enriched coating; the third coating (applied over and contacting the second coating) can comprise a hard sugar phytochemical-enriched coating; the fourth coating (applied over and contacting the third coating) can comprise a hard sugar enzyme-enriched coating; and, the fifth coating (applied over and contacting the fourth coating) can comprise a hard sugar coating substantially free of any vitamins, enzymes, phytochemicals, and ailmentary vegetable compositions. Each coating containing vitamins, enzymes, phytochemicals, and/or ailmentary vegetable compositions and is preferably, but not necessarily, free of minerals, particularly minerals which promote the degradation of the vitamins, enzyme, phytochemicals, and ailmentary vegetable compositions. Each coating which does not contain vitamins, enzymes, phytochemicals, and/or ailmentary vegetable compositions is also preferably, but not necessarily, free of minerals, especially minerals which promote the degradation of vitamins, enzymes, phytochemicals, and/or ailmentary vegetable compositions contained in adjacent coatings on the gum composition or on the candy center. A coating which does not contain vitamins (or enzymes or phytochemicals or ailmentary vegetable compositions) can be utilized in between two different coatings containing vitamins (or containing enzymes or phytochemicals or ailmentary vegetable compositions). A coating containing oxygen sensitive vitamins, enzymes, phytochemicals, or ailmentary vegetable compositions can be placed nearer to the gum core or candy center and further from the outermost coating on the gum core or candy center. A coating containing water sensitive vitamins, enzymes, phytochemicals, or ailmentary vegetable compositions can be placed nearer to the outermost coating on the gum core or candy center and further away from the gum core or candy center. One of the outer coatings on a gum core or candy center can include substances like ascorbyl palmitate or vitamin E which "scavenge" and combine with oxygen to protect oxygen sensitive vitamins, enzymes, phytochemicals, or ailmentary vegetable compositions which are in a coating which is closer to the gum core or candy center and is further away from the outer surface of the coated gum core or candy center. Ascorbyl palmitate can be utilized in the gum core or the candy center to prevent oxidation. One of the outer coatings on a gum core or candy center can include a substance(s) which insulates from heat, light, or static electricity coatings which are closer to the coated gum core or candy center and are further away from the outer surface of the coated gum core or candy center. One of the outer coatings on a gum core or candy center can include a substance(s) which absorbs and binds water to protect from moisture coatings which are closer to the gum core or candy center and farther from the outer surface of the coated gum core or coated candy center.

As used herein, a "layer" in a coating has substantially the same composition as any other layer in the coating, i.e., a coating comprises one or more sequential layers each having substantially the same composition. For example, three layers which are sequentially formed on a gum core or candy center by utilizing the same syrup composition (for example, the syrup composition of Example 2) collectively comprise a coating. When, however, a single layer of the syrup of Example 2 is applied to a gum core or candy center, followed by a single vitamin enriched syrup layer, then the single layer of the syrup of Example 2 comprises a first coating, and the single vitamin enriched syrup layer comprises a second coating which has a composition different from that of the first coating.

As used herein, a coating "seals" an adjacent coating from moisture, minerals, etc. in the gum core or candy center when (1) it (the "sealing" coating) is intermediate the adjacent coating and the gum core or candy center, and (2) it (the "sealing" coating) reduces the penetration of moisture and minerals into the adjacent coating in comparison to the penetration which occurs when the adjacent coating directly contacts the gum core or candy center. Further, a coating "seals" an adjacent coating from oxygen when (1) it (the sealing coating) is intermediate the adjacent coating and the ambient air, and (2) it (the sealing coating) reduces the penetration of oxygen into the adjacent coating in comparison to the penetration which occurs when the adjacent coating directly contacts the ambient air. Vitamins, enzymes, phytochemicals, proteins, and ailmentary vegetable compositions can each comprise from about 0.0001% to about 50%, preferably from about 0.001% to about 4.0%, by weight of a coating on a gum pellet or soft candy composition center. The chewing gum composition can include from about 1% to 50% by weight moisture (i.e., water), and preferably includes from about 5% to 15% by weight moisture. The amount of moisture in the soft candy center can vary from about 1% to 95% by weight, but preferably is in the range of about 5% to 40% by weight. If desired, from about 0.001% to 15%, preferably about 0.1% to 3.0%, by weight of ascorbyl palmitate can be utilized in a gum or candy center or in a coating on one of said centers.

Having described my invention in such terms as to enable those skilled in the art to understand and practice it and having identified the presently preferred embodiments thereof, I claim:

1. A coated confection product including
   (a) a soft candy composition including 5% to 40% by weight moisture;
   (b) a first outer coating on said soft candy composition and containing at least one vitamin selected from the group consisting of vitamin A, vitamin B, vitamin C, vitamin D, vitamin E, vitamin K, and vitamin P; and
   (c) a second outer coating intermediate said soft candy composition and said first outer coating to sealingly separate said vitamin from the moisture in said soft candy composition.

2. The coated confection product of claim 1 wherein said first outer coating is substantially free of minerals which promote the degradation of said vitamin.

3. The confection product of claim 1 including ascorbyl palmitate in said soft candy composition.

4. The confection product of claim 1 including in said first outer coating at least one phytochemical.

5. The confection product of claim 1 including in said first outer coating at least one enzyme.

6. The confection product of claim 1 including in said first outer coating at least one ailmentary vegetable composition.

7. A coated confection product including
   (a) a soft candy composition including 5% to 40% by weight moisture;
   (b) a first outer coating on said soft candy composition and containing at least one enzyme, and
   (c) a second outer coating intermediate said composition and said first outer coating to sealingly separate said enzyme from the moisture in said soft candy composition.

8. The coated confection product of claim 7 wherein said first outer coating is substantially free of minerals.

9. The confection product of claim 7 including ascorbyl palmitate in said soft candy composition.

10. The confection product of claim 7 wherein said enzyme promotes the cleansing of teeth.

11. The confection product of claim 7 wherein said enzyme promotes the digestion of vitamins by the human body.

12. The confection product of claim 7 wherein said enzyme promotes the digestion of minerals by the human body.

13. The confection product of claim 7 wherein said enzyme promotes the cleansing of the oral cavity.

14. A coated confection product including
   (a) a soft candy composition including 5% to 40% by weight moisture;
   (b) a first outer coating on said composition and containing at least one phytochemical, and
   (c) a second outer coating intermediate said composition and said first outer coating to sealingly separate said phytochemical from the moisture in said soft candy composition.

15. The coated confection of claim 14 wherein said first outer coating is substantially free of minerals.

16. The confection product of claim 14 including ascorbyl palmitate in said soft candy composition.

17. A coated confection product including
   (a) a soft candy composition including 5% to 40% by weight moisture;
   (b) a first outer coating on said composition and containing at least one ailmentary vegetable composition; and,
   (c) a second outer coating intermediate said composition and said first outer coating to sealingly separate said ailmentary vegetable composition from the moisture in said soft candy composition.

18. The coated confection product of claim 17 wherein said first outer coating is substantially free of minerals.

19. The confection product of claim 17 including ascorbyl palmitate in said soft candy composition.

20. A method for autogenously administering vitamins to a human subject concurrently with the use of candy, comprising the steps of:

(a) forming a coated confection product including
   (i) a soft candy composition including 5% to 40% by weight moisture,
   (ii) a first substantially mineral free outer coating on said soft candy composition and containing at least one vitamin, and
   (iii) a second outer coating intermediate said soft candy composition and said first outer coating to sealingly separate said vitamin from said moisture in said soft candy composition; and,
(b) administering the coated confection product in the mouth of the subject to be chewed to release said vitamin from said first outer coating.

21. A method for autogenously administering enzymes to a human subject concurrently with the use of candy, comprising the steps of:
(a) forming a coated confection product including
   (i) a soft candy composition including 5% to 40% by weight moisture,
   (ii) a first substantially mineral free outer coating on said soft candy composition and containing at least one enzyme, and
   (iii) a second outer coating intermediate said soft candy composition and said first outer coating to sealingly separate said enzyme from said moisture in said soft candy composition; and,
(b) administering the coated confection product in the mouth of the subject to be chewed to release said enzyme from said first outer coating.

22. The method of claim 21 wherein said enzyme is selected from the group consisting of alpha amylase, protease, beta glucanase, glucoamylase, glucose oxidase, pectinase, xylanase, protein hydrolyzing enzymes, starch dextrinizing enzymes, starch saccharifying enzymes, and cellulose hydrolyzing enzymes.

23. The method of claim 21 wherein said enzyme promotes the cleansing of teeth.

24. The method of claim 21 wherein said enzyme promotes the digestion of vitamins by the human body.

25. The method of claim 21 wherein said enzyme promotes the digestion of minerals by the human body.

26. The method of claim 21 wherein said enzyme promotes the cleansing of the oral cavity.

* * * * *